(12) United States Patent
Gee

(10) Patent No.: US 9,387,227 B2
(45) Date of Patent: Jul. 12, 2016

(54) METHOD FOR TREATMENT OF SORES AND LESIONS OF THE SKIN

(71) Applicant: Gilbert Clinton Gee, Orlando, FL (US)

(72) Inventor: Gilbert Clinton Gee, Orlando, FL (US)

(73) Assignee: Gilbert Clinton Gee, Orlando, FL (US)

( * ) Notice: Subject to any disclaimer, the term of this patent is extended or adjusted under 35 U.S.C. 154(b) by 0 days.

(21) Appl. No.: 14/845,580

(22) Filed: Sep. 4, 2015

(65) Prior Publication Data

US 2015/0374759 A1      Dec. 31, 2015

Related U.S. Application Data

(63) Continuation of application No. 10/602,404, filed on Jun. 23, 2003, now abandoned.

(51) Int. Cl.
| | | |
|---|---|---|
| *A61K 35/644* | (2015.01) | |
| *A61K 31/522* | (2006.01) | |
| *A61K 31/70* | (2006.01) | |
| *A61K 36/00* | (2006.01) | |
| *A61K 36/74* | (2006.01) | |

(52) U.S. Cl.
CPC ............. *A61K 35/644* (2013.01); *A61K 31/522* (2013.01); *A61K 31/70* (2013.01); *A61K 36/00* (2013.01); *A61K 36/74* (2013.01)

(58) Field of Classification Search
CPC ... A61K 2300/00; A61K 36/23; A61K 31/51; A61K 31/525; A61K 31/714; A61K 36/05; A61K 36/31; A61K 36/34; A61K 36/48; A61K 36/534; A61K 36/63; A61K 36/899; A61K 31/4166; A61K 36/185; A61K 9/0056; A61K 35/644; A61K 9/7007; A61K 31/045; A61K 31/353; A61K 33/40; A61K 36/82; A61K 31/192; A61K 31/7048; A61K 31/352; A61K 36/22; A61K 45/06; A61K 31/7028; A61K 31/7034; A61K 31/7024; A61K 31/05; A61K 31/35

See application file for complete search history.

(56) References Cited

U.S. PATENT DOCUMENTS

| | | | | |
|---|---|---|---|---|
| 5,382,436 | A * | 1/1995 | Potts | A61K 31/52 424/445 |
| 5,952,373 | A * | 9/1999 | Lanzendorfer | A61K 8/36 514/152 |
| 6,953,574 | B2 * | 10/2005 | Sobol | A23C 9/133 424/439 |
| 2003/0086986 | A1 * | 5/2003 | Bruijn | A61K 9/0048 424/729 |

OTHER PUBLICATIONS

White et al, The Herbal Drugstore, Part III, Coldsores, , pp. 171-172, 2000.*

* cited by examiner

*Primary Examiner* — Debbie K Ware
(74) *Attorney, Agent, or Firm* — Coats & Bennett, PLLC

(57) ABSTRACT

A composition for the topical treatment of sores, lesions, ulcers, and other disorders of the skin, said composition includes a combination of a bee product and caffeine. The bee product may comprise bee pollen, bee propolis, honey, or royal jelly. Variations of the composition may also contain a tannin. The composition may be in the form of an ointment or cream that is applied topically to an affected area of the body. The composition may also be used in other forms, such as a spray, shampoo, soap, lipstick, or adhesive bandage. The invention may also be useful as a health beverage.

10 Claims, No Drawings

METHOD FOR TREATMENT OF SORES AND LESIONS OF THE SKIN

RELATED APPLICATIONS

This application is a Continuation application, and claims priority from the co-pending application having application Ser. No. 10/602,404, now abandoned. The '404 application, which is entitled "Method for Treatment of Sores and Lesions of the Skin," was filed on Jun. 23, 2003, and is incorporated herein be reference in its entirety.

FIELD OF THE INVENTION

The present invention relates generally to methods for treatment of sores and skin lesions and, more particularly, to methods for treating sores and lesions associated with Herpes Simplex Virus.

BACKGROUND OF THE INVENTION

Herpes Simplex Virus (HSV) is a common cause of infections of the skin and mucus membranes. HSV is one of the most difficult viruses to control and has plagued mankind for thousands of years. HSV infection is typically manifested by painful, blister-like lesions or sores on the mouth or face (oral herpes) or in the genital area (genital herpes). While rarely fatal, herpes sores can be quite painful and unsightly and may cause embarrassment to the infected person.

There are two distinct types of Herpes Simplex Virus, Herpes Simplex Virus 1 (HSV-1) and Herpes Simplex Virus 2 (HSV-2). HSV-1 and HSV-2 are very similar. They can occur separately or can infect the same individual. HSV-1 is generally associated with oral herpes and HSV-2 is generally associated with genital herpes. It is now known, however, that HSV-2 can cause oral herpes and HSV-1 can cause genital herpes.

HSV enters the body through the skin or mucus membranes following contact with an infected person. The virus penetrates vulnerable cells in the lower layers of the skin and attempts to replicate itself in the cell nuclei. In many cases, HSV never causes symptoms to occur. However, if HSV's replication process destroys the host cells, symptoms in the form of sores, ulcers, and fluid-filled blisters may appear. The sores from the primary infection eventually heal without scarring. However, the virus that caused the infection remains in the body and migrates through branches of nerve cells to clusters at the nerve cell ends called the ganglia. The virus persists in the ganglia in a latent state, during which viral replication does not occur. While the virus is latent, symptoms of the virus do not appear. After remaining dormant for some time, the virus may again begin to replicate, causing a recurrent infection. Recurrent infections of HSV tend to be milder than primary infections and can be set off by a variety of factors, including illness and stress. For some persons infected with herpes virus, recurrent infections may be frequent. Approximately 20% to 40% of persons with HSV-1 experience recurrent outbreaks. For persons infected with HSV-2, the recurrence rate is up to 80%.

Scientists are getting closer to decoding the genetic structure of herpes virus. At the present time, however, there is no known cure for herpes. Therefore, there remains a need for new drugs and therapies that ameliorate the symptoms of recurrent outbreaks of HSV.

BRIEF SUMMARY OF THE INVENTION

The present invention comprises a pharmaceutical composition for topical application to treat sores, ulcers, lesions, or other disorders of the skin. The composition has been found to be effective for treatment of sores associated with Herpes Simplex Virus. The composition may also be useful for treatment of chicken pox, shingles, or other skin disorders resulting from viral infections.

The active ingredients of the composition comprise a combination of a bee product and caffeine. The bee product may, for example, comprise honey, bee propolis, bee pollen, or royal jelly. Variations of the composition may also include tannin as an active ingredient. The composition may be in the form of a cream, ointment, or gel that is applied topically to the skin. The composition may also be used in other forms, such as a spray, shampoo, soap, lipstick, or adhesive bandage. The invention may also be useful as a health beverage.

DETAILED DESCRIPTION OF THE INVENTION

The present invention comprises compositions for topical application to the skin including as active ingredients a combination of a bee product and caffeine. The bee product may, for example, comprise honey, bee propolis, bee pollen, or royal jelly. As scientist obtain a better understanding of the how composition works against HSV, compositions according to the present invention may be formed with active ingredients extracted from honey or other bee products, or with active ingredients synthesized to resemble the active ingredients in honey or bee products. Thus, the term bee product as used herein includes active ingredients extracted from bee products and active ingredients synthesized to resemble the active ingredients in bee products. Variations of the composition may also include a tannin as an active ingredient.

In one exemplary embodiment, a salve was prepared comprising a mixture of honey (preferably raw) and coffee grounds. The salve was prepared by combining approximately one tablespoon of coffee grounds with enough honey to hold the grounds together. It is estimated that the salve comprised approximately 15% by weight of honey. The salve was applied to sores of one patient caused by type I herpes simplex virus by spreading the salve over the sores and covering the sores with a bandage. Following application of the salve to the sores, the sores were reduced significantly in size within 3 to 4 hours and the sores were completely healed within 2 days. Prior to treatment with the anti-HSV composition, the patient experienced recurring infections once or twice a month. Following treatment, the patient has not had a single recurrence of the infection after more than five months.

Compositions according to the present invention may be made using micronized caffeine particles as described in U.S. Pat. No. 5,382,436, which is incorporated herein by reference. Further studies are needed in order to determine the amount of caffeine and bee product that is most efficacious. At present, the inventor believes that compositions containing greater than 1% by weight of caffeine would be effective.

The stickiness of honey makes it inconvenient for topical application. Therefore, the composition may include, in addition to the active agents, a pharmaceutically acceptable excipient. Additives such as oils, thickening agents and emulsifiers may be used to form an ointment, cream, lotion or gel that is more suitable for topical application. Examples of natural oils that may be used include corn oil, almond oil, olive oil, coconut oil, caster oil, and lanolin oil. Synthetic oils, such as silicone oil may also be used. Possible thickening agents include natural waxes such as beeswax, paraffin waxes, and hydrocarbon polymers. U.S. Pat. No. 6,171,604, which is incorporated herein by reference, describes various honey-based preparations for topical application. Preparations described in this patent may be used with the present invention.

The composition may be formed into an ointment, cream, salve, lotion, or gel that is applied topically to the skin. The composition may also be used in other forms, such as a spray, shampoo, soap, or lipstick. Another use of the present invention is in adhesive bandages having an absorbent pad that can be applied to the skin. Mixtures of caffeine and honey may also have use in health beverages that can be ingested. Beverages may be used to prevent outbreaks of HSV or other illnesses, or may be ingested to lessen the effect of an outbreak.

The mechanism by which the composition inhibits HSV infection is not known. Caffeine closely resembles adenosine and will bind to adenosine receptors. It is possible that the caffeine binds to virus receptors used by the HSV and thereby inhibits the replication of HSV. Bee pollen, bee propolis, and bee honey are known to have antioxidant, antibiotic and antifungal properties. Bee products have been used in the past as home remedies for treatment of wounds, canker sores, mouth ulcers and herpes. Bee propolis, which is present in honey, contains caffeic acid phenethyl ester (CAPE). Studies conducted in the past show that CAPE suppresses the growth of cancerous cells and may, therefore, act as an anti-tumor agent. In laboratory cultures, propolis has been shown to inhibit the growth of some viruses including herpes and influenza. Tannins are naturally occurring plant polyphenols which combine with protein and other polymers to form stable compounds. Some tannins are known to have antiseptic, antibiotic and antiviral properties. Tannins at relatively high concentrations can inhibit the activity of enzymes. Some tannins also show strong antitumor activity.

In recent years, combined therapies have become increasingly popular in combating HSV and research has shown that certain drugs may enhance the effect of other drugs to produce not only an additive but also a synergistic effect. Combined therapies known to be effective for treatment of herpes include trifluorothymidine (TFT) with interferon-alpha, caffeine with interferon, and dimethyl sulfoxide (DMSO) with idoxuridine (IDU). It is suspected that the combination of a bee product and caffeine produces such a synergistic effect that inhibits replication of the virus more so than would treatment with either caffeine or bee product alone. Tannin may also play a role in retaining the active ingredients in honey and caffeine in the lower layers of the skin to prevent recurrence of HSV.

The composition is useful for the treatment of sores and lesions caused by herpes simplex virus, and may also be useful for the treatment of chicken pox, shingles or other viral infections.

What is claimed is:

1. A method for treating a person having a viral infection, the method comprising:
    mixing honey and coffee grounds to form a salve comprising approximately 15% by weight of honey, wherein the salve further comprises tannin;
    and
    topically applying the salve to a sore caused by a the viral infection to lessen an effect of an outbreak of the viral infection.

2. The method of claim 1 further comprising bandaging the sore after the salve has been applied to the sore.

3. The method of claim 1 wherein the step of topically applying the salve to the sore caused by the viral infection comprises applying an absorbent pad containing the salve to the sore.

4. The method of claim 1 further comprising mixing an oil-based additive with the honey and coffee grounds into the salve.

5. The method of claim 1 further comprising mixing a thickening agent with the honey and coffee grounds into the salve.

6. A method for treating a person having a viral infection, the method comprising: mixing honey, coffee ground, and tannin to form a salve comprising approximately 15% by weight of honey; and topically applying the salve to a sore caused by a the viral infection to lessen an effect of an outbreak of the viral infection.

7. The method of claim 6 further comprising bandaging the sore after the salve has been applied to the sore.

8. The method of claim 6 wherein the step of topically applying the salve to the sore caused by the viral infection comprises applying an absorbent pad containing the salve to the sore.

9. The method of claim 6 further comprising mixing an oil-based additive with the honey and coffee grounds into the salve.

10. The method of claim 6 further comprising mixing a thickening agent with the honey and coffee grounds into the salve.

* * * * *